(12) United States Patent
Bourne et al.

(10) Patent No.: US 11,559,262 B2
(45) Date of Patent: Jan. 24, 2023

(54) OPERATION AND CONTROL OF MAGNETIC RESONANCE IMAGING APPARATUS

(71) Applicant: Elekta Limited, West Sussex (GB)

(72) Inventors: Duncan Bourne, Surrey (GB); Anthony Williams, West Sussex (GB)

(73) Assignee: Elekta Limited, Crawley (GB)

( * ) Notice: Subject to any disclaimer, the term of this patent is extended or adjusted under 35 U.S.C. 154(b) by 510 days.

(21) Appl. No.: 16/179,175

(22) Filed: Nov. 2, 2018

(65) Prior Publication Data
US 2019/0133538 A1    May 9, 2019

(30) Foreign Application Priority Data
Nov. 3, 2017 (GB) .................................... 1718288

(51) Int. Cl.
*A61B 5/055*    (2006.01)
*G01R 33/54*    (2006.01)
(Continued)

(52) U.S. Cl.
CPC .......... *A61B 5/7445* (2013.01); *A61B 5/0036* (2018.08); *A61B 5/055* (2013.01);
(Continued)

(58) Field of Classification Search
CPC ................................ A61B 5/055; A61N 5/10
See application file for complete search history.

(56) References Cited

U.S. PATENT DOCUMENTS

| | | | | |
|---|---|---|---|---|
| 4,710,947 A | * | 12/1987 | Klein | ........................ A61B 6/06 211/85.13 |
| 2002/0068862 A1 | * | 6/2002 | Kleiman | ................ A61B 6/467 600/407 |

(Continued)

FOREIGN PATENT DOCUMENTS

| | | | |
|---|---|---|---|
| JP | 59015937 Y2 | * | 5/1984 |
| WO | WO 2014/087557 A1 | | 6/2014 |

OTHER PUBLICATIONS

United Kingdom Intellectual Property Office, Combined Search and Examination Report, Application No. GB1718288.2, dated Apr. 19, 2018, 6 pages.

*Primary Examiner* — Colin T. Sakamoto
(74) *Attorney, Agent, or Firm* — Schwegman Lundberg & Woessner, P.A.

(57) ABSTRACT

A combined MRI and radiotherapy apparatus comprises a radiotherapeutic source, an MRI system, a patient support, drive motors for the patient support arranged to adjust the position of the patient support while a patient is on the support, a control panel having a user-operable input interface for controlling the drive motors, and a display unit. A mounting arrangement for a display device comprises a transparent cover, a display panel held against a rear face of the cover so as to be visible through a front face of the cover, and a retaining structure for holding the display panel in place. The retaining structure comprises a chassis fixable in position relative to the cover, the chassis having at least one resilient finger extending therefrom alongside a rear face of the display panel, a part of which bears against the rear face of the display panel to resiliently urge the display panel against the rear face of the cover. The radiotherapeutic source, MRI system, patient support and the control panel will usually be located within an enclosed space, to confine the therapeutic radiation; a second control panel is provided (Continued)

outside the enclosed space, able to control at least the radiotherapy source.

20 Claims, 5 Drawing Sheets

(51) Int. Cl.
    *G01R 33/48*     (2006.01)
    *A61N 5/10*     (2006.01)
    *A61B 5/00*     (2006.01)
    *G06F 3/0488*     (2022.01)

(52) U.S. Cl.
    CPC .............. *A61B 5/7475* (2013.01); *A61N 5/10* (2013.01); *A61N 5/1048* (2013.01); *G01R 33/4808* (2013.01); *G01R 33/546* (2013.01); *A61N 2005/1074* (2013.01); *A61N 2005/1092* (2013.01); *G06F 3/0488* (2013.01)

(56) References Cited

U.S. PATENT DOCUMENTS

| | | | | |
|---|---|---|---|---|
| 2005/0117290 A1* | 6/2005 | Chen | ...................... | G06F 1/184 361/679.02 |
| 2008/0158445 A1* | 7/2008 | Yokawa | ................... | H04N 5/64 348/836 |
| 2012/0281381 A1* | 11/2012 | Sanford | ................ | G06F 1/1637 361/807 |
| 2014/0275963 A1* | 9/2014 | Shvartsman | ........... | A61B 5/055 600/411 |
| 2014/0299025 A1 | 10/2014 | Moita | | |
| 2015/0297148 A1* | 10/2015 | Biber | ..................... | A61B 5/055 600/418 |
| 2016/0367142 A1* | 12/2016 | Hardie | ................. | A61B 5/0046 |
| 2017/0234947 A1* | 8/2017 | Kim | ................. | G01R 33/34076 324/322 |
| 2017/0285118 A1* | 10/2017 | Kim | ................. | G01R 33/34076 |
| 2018/0083322 A1* | 3/2018 | Pakula | ................... | H05K 1/144 |
| 2018/0271463 A1* | 9/2018 | Maciejewski | .......... | A61B 6/462 |

* cited by examiner

OPERATION AND CONTROL OF MAGNETIC RESONANCE IMAGING APPARATUS

CROSS-REFERENCE TO RELATED PATENT APPLICATIONS

This patent application claims priority to United Kingdom patent application no. 1718288.2 filed on Nov. 3, 2017, the entire contents of which are hereby incorporated by reference.

FIELD OF THE INVENTION

The present invention relates to the operation and control of magnetic resonance imaging devices.

BACKGROUND ART

Magnetic Resonance Imaging ("MRI") devices operate by establishing a fixed, steady magnetic field, together with a variable gradient field, applying a radio-frequency ("rf") signal to the volume being investigated, and detecting an rf response. They therefore need to operate in an environment that is free from sources of rf interference.

External-beam radiotherapeutic apparatus operates by directing a shaped beam of radiation towards a tumour from multiple directions. The beam is emitted from a source that is mounted on a gantry so that it is rotatable around a central axis, with the beam being directed radially inwards towards a defined point on the axis known as the isocentre. Thus, a tumour placed at the isocentre can remain in the beam throughout the treatment (if desired), whereas healthy tissue around the tumour and spaced from the isocentre will only receive a brief irradiation as the beam passes. In practice, the beam can be collimated and controlled according to a treatment plan so as to build up a desired three-dimensional dose distribution within the patient corresponding to the tumour shape.

The beam is usually made up of high-energy x-rays at typically over 1 Mev, and therefore careful precautions need to be taken in order to ensure that it is properly collimated, that the attenuated beam (i.e. after transmission through the patient) is absorbed, and that scattering is minimised. The operator will usually leave the room during treatment in order to limit their cumulative exposure to scattered radiation.

Recently, combined MRI and radiotherapeutic devices have been proposed. The MR coils are separated into two sections spaced along the axis of the device, with a gap between them through which the beam is directed. This has the potential to allow high-quality diagnostic images of the patient to be prepared in situ immediately prior to treatment or during treatment.

One design of such a combined device uses a linear accelerator as the radiotherapeutic source, movable on a circular path around a central horizontal axis. The MRI magnet structures are located concentrically within the circular path, around the same axis. An example is shown and described in our earlier application WO2012/076150.

SUMMARY OF THE INVENTION

As such devices become available, it will be necessary to reconsider the workflows and protocols for their use. For example, in an MRI unit there is no need for the operator to leave the room during imaging. They may do so, for reasons of convenience, but it is not essential and it is by no means uncommon for staff or family to remain with patients who need comfort or assistance. Further, as an imaging modality it is not strictly necessary for the patient to be positioned precisely when being placed in an MRI apparatus, so long as the relevant part of the patient is within the imagable volume of the device.

However, in a radiotherapy device there is a positive need for staff to leave the treatment room during treatment, as noted above. Also, as a treatment modality with a defined isocentre, it is usual for patients to be positioned within a radiotherapeutic apparatus with a considerable degree of accuracy. Typically, therefore, the clinical staff will assist the patient onto the device, and position them on a couch or the like. The couch often has controls allowing it to be positioned in 6 degrees of freedom (three translational and three rotational) so that the patient position is correct. Feedback systems may be provided, such as laser markers which must be aligned with markings applied to the patient's skin.

The present invention provides a mounting arrangement for a display device, comprising a transparent panel, a display device held against a rear face of the panel so as to be visible through a front face of the panel, and a retaining structure for holding the display device in place, the retaining structure comprising a chassis fixable in position relative to the panel behind the display device, and having at least one resilient finger extending therefrom alongside a rear face of the display device, a part of which bears against the rear face of the display device to resiliently urge the display device against the rear face of the panel.

The display device can be a touch-screen device. Alternatively, or in addition, the display device may be a control panel.

This mounting arrangement can be used in the above context, or in any other context where a touch-screen device needs to be mounted behind a protective transparent panel. It maintains the necessary close relationship between the front face of the touchscreen device and the transparent panel so as to allow the touchscreen functionality to work. Typically, this would otherwise be achieved by adhesively fixing the touchscreen device in place; this achieves the immediate aim of securing the touchscreen in place but makes subsequent replacement of the touchscreen device extremely difficult or impossible to do without replacing the transparent pane as well.

The mounting arrangement may include at least one finger. Said finger may include a protrusion which bears on the rear face of the display panel. The protrusion may be located at an end part of the finger. The protrusion typically has a depth greater than the spacing between the chassis and the rear face of the display panel when the chassis and display panel are mounted.

The chassis may comprise a plurality of fingers. We prefer that the fingers are arranged in a symmetrical pattern to evenly distribute the biasing force to the extent of the rear face of the display panel to evenly bias the touch screen device against the rear face of the panel.

We prefer that the chassis of the mounting arrangement is a plate for ease of manufacture. The or each finger may be formed as a part of the plate and defined by an arcuate slot formed therein. The slot is typically U-shaped.

The transparent panel of the mounting arrangement will typically be glass or polycarbonate. We prefer the chassis to be held such that the frame supports the display panel in at least a direction parallel to the plane of the cover.

The present invention further provides a combined MRI and radiotherapy apparatus comprising a display panel wherein the control display panel is mounted using the mounting arrangement described.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
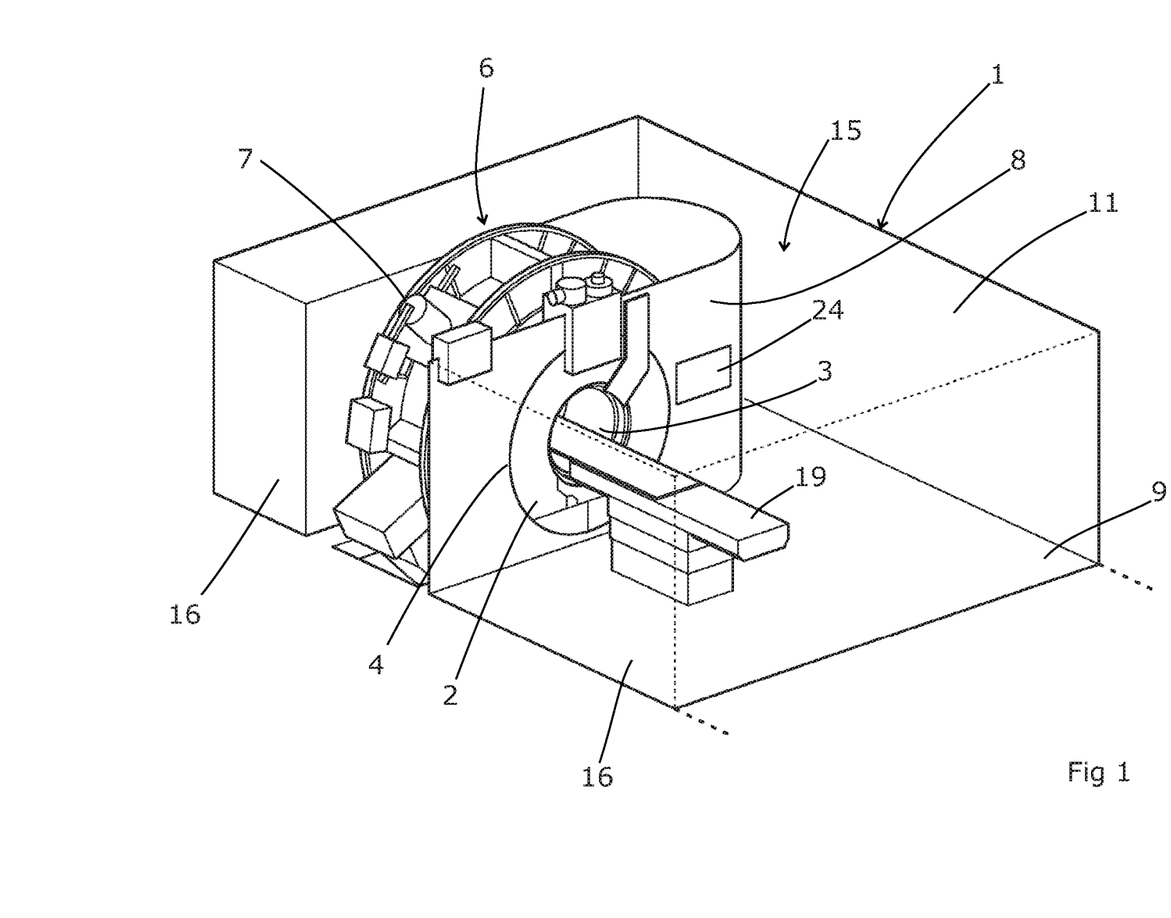
FIG. 1 shows a perspective view of an exam room of a magnetic resonance imaging system with an additional linac device according to a general setup.

FIG. 1 shows a general setup of an examination room 1 of a combined magnetic resonance (MR) imaging and radiotherapeutic imaging and treatment system 6. The general setup of the MR imaging system 2 comprises an examination tube 3, a main magnet 4 and a gradient coil assembly 5, whereby the main magnet 4 and the gradient coil assembly 5 are located to surround the examination tube 3, as can be best seen in FIGS. 2 and 3.

The MR imaging system 2 is part of an imaging and treatment system 6 comprising an additional radiotherapeutic device in the form of a linear accelerator and x-ray source 7, which is operated together with the MR imaging system 2. The radiotherapeutic device 7 is located at an outer circumference of the main magnet 4.

The exam room 1 has an exam room shielding 10 for electromagnetically shielding the MR imaging system 2. Accordingly, the exam room shielding 10 is made of an electrically conductive material. The exam room shielding 10 comprises a ceiling, which is not shown in the figures, a floor 9 of the exam room 1, side walls 11 interconnecting the ceiling and the floor 9. The side walls 11 of the exam room shielding 10 form the outline of a U-shaped room 15 with fascia 8 of the imaging and treatment system 6 connecting the lateral flanks 16 to define a U-shape. The longitudinal ends 13 of the examination tube 3 of the magnetic resonance imaging system 2 interconnect the lateral flanks 16 of the U-shaped room 15. Internal door 22 completes the electromagnetic shield.

Of course, the structure need not adopt the actual side walls of the space in which the installation is placed. If preferred, the room walls 11 can be false walls within that space. The exam room may be defined by structural walls integral to the fabric of the building. These walls may comprise isolating concrete slab to surround the imaging and treatment rooms. The isolating slab typically comprises a reinforced load bearing floor slab. The ceiling and walls are typically comprised of concrete slab designed for acoustic and vibration isolation to aid MRI function and to contain x-ray scatter. Lead lining can be provided to provide additional containment of x-ray scatter from the x-ray source 7. On the one hand, there is a clear incentive to take advantage of the maximum available space, but on the other hand it may be easier or more economic to construct prefabricated sections for the room walls 11.

For reasons of aesthetics, durability and comfort, it may be preferable to conceal at least part of the ceiling and/or floor shielding with tiles suitable for ceiling and floor use. Such tiles are widely available.

The U-shaped room 15 is provided with operational spaces 17, which are located in front of the longitudinal ends 13 of the examination tube 3. The U-shaped room 15 is provided with a walkway 18 between the operational spaces 17, which is the base of the U-shaped room 15 in this embodiment. An examination table 19 is located inside the exam room shielding 10, so that a patient lying on this examination table 19 can be moved from one operational space 17 into the examination tube 3 and vice versa.

An ante-room 20 (FIGS. 2 and 3) is located immediately outside the examination room 1. An access door 21 allows patients and staff to enter the ante-room 20, and an internal door 22 allows access from the ante-room 20 into the examination room 1. There is no other access to the examination room 1, so staff in the ante-room 20 control all access to the examination room 1 and can be confident as to how many people are present.

Figure 2:
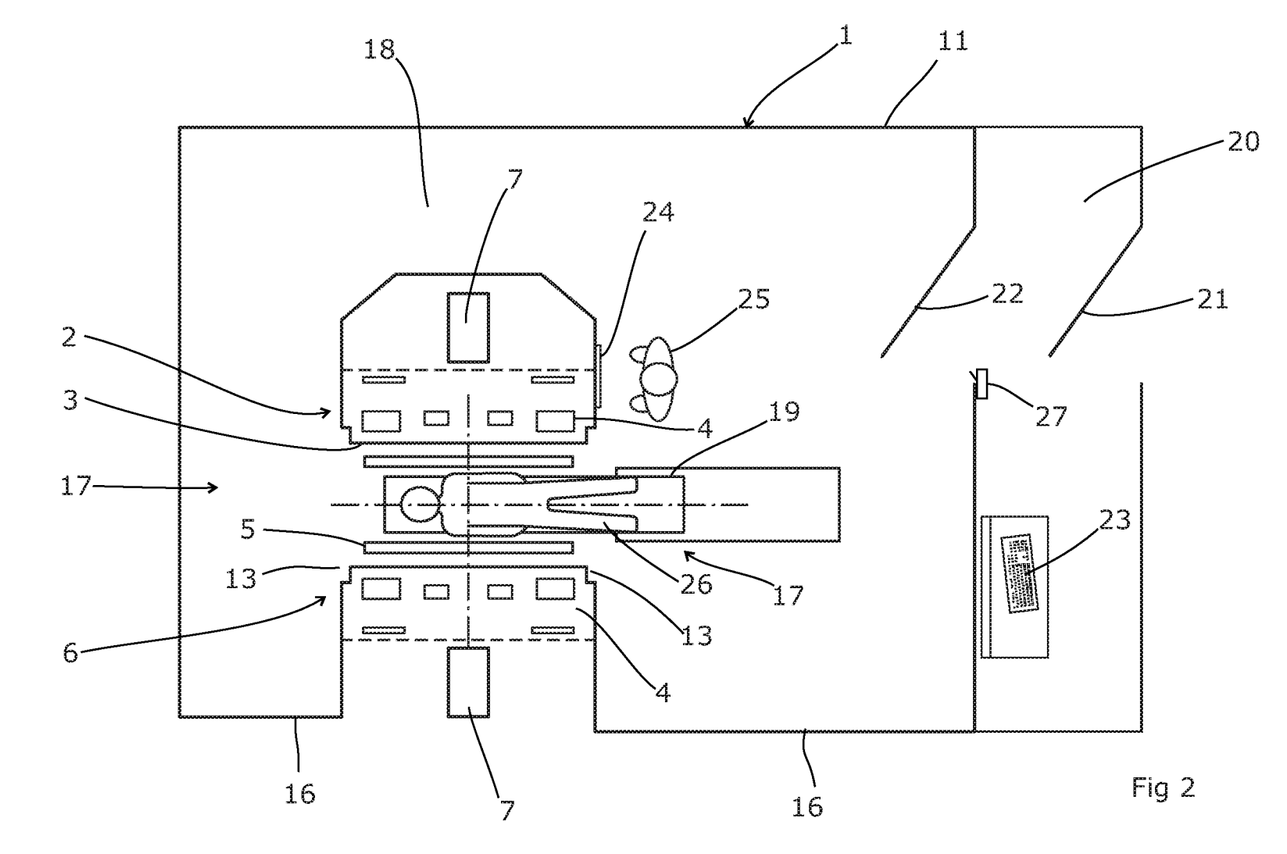
FIG. 2 schematically shows a detailed top view of the general exam room of FIG. 1, during a setting-up stage, FIG. 3 schematically shows a detailed top view of the general exam room of FIG. 1 during a treatment stage.
Figure 3:
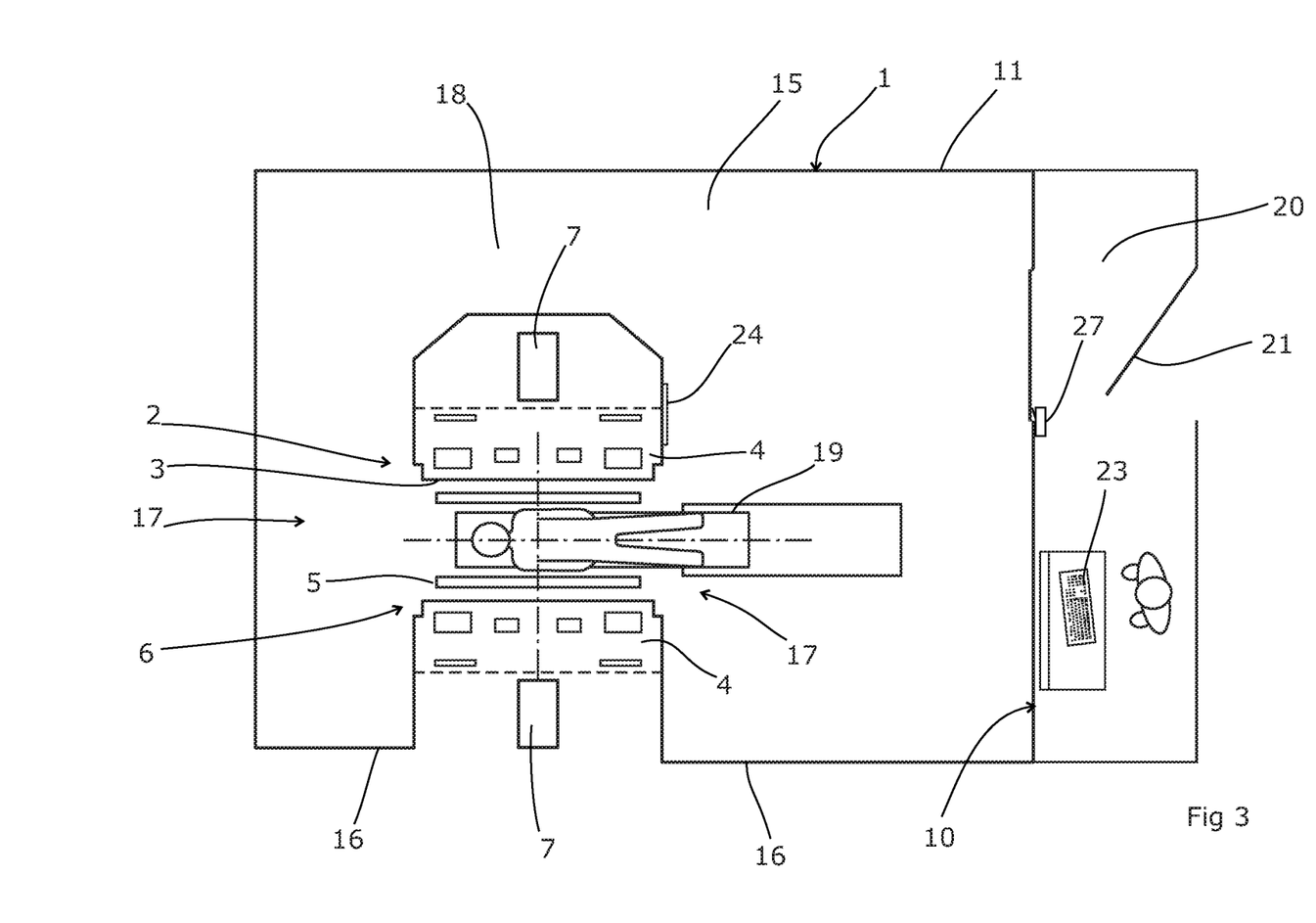

Control of the apparatus is in two forms. A main control terminal 23 is located in the ante-room 20 and controls substantially all functions of the apparatus, including the radiotherapy apparatus and the MRI functions. In addition, a display panel, here a touch-screen control panel 24, is provided within the examination room 1 to provide control over the functions relating to the patient table 19 and (in particular) its positioning. As illustrated in FIGS. 1 to 3, the touch-screen control panel 24 is located on a side wall of the imaging and treatment system 6 adjacent to the examination tube 3 so that it is conveniently to hand while a member of staff 25 (FIG. 2) is assisting a patient 26 into the device. The touchscreen displays a user interface allowing adjustment of the patient table 19 in two or three translational dimensions, and potentially also three rotational dimensions if desired, in order to allow the table 19 to be lowered for the patient 26 to lie down on its surface, with or without assistance, be raised to let the member of staff 25 assist the patient in positioning themselves comfortably and correctly, raise further (if necessary) to align with the examination tube 3, and then slide horizontally into the examination tube 3. This allows precise positioning of the patient 29 within the examination tube 3 and relative to the x-ray source 7. Feedback can be provided to the staff member, such as the patient's identity information for checking purposes, and/or the intended configuration for the device, such as the pattern of footrests, supports etc for the patient. Thus, the staff member 25 can easily guide the patient 26 into an accurate position, ready for treatment.

Figure 4:
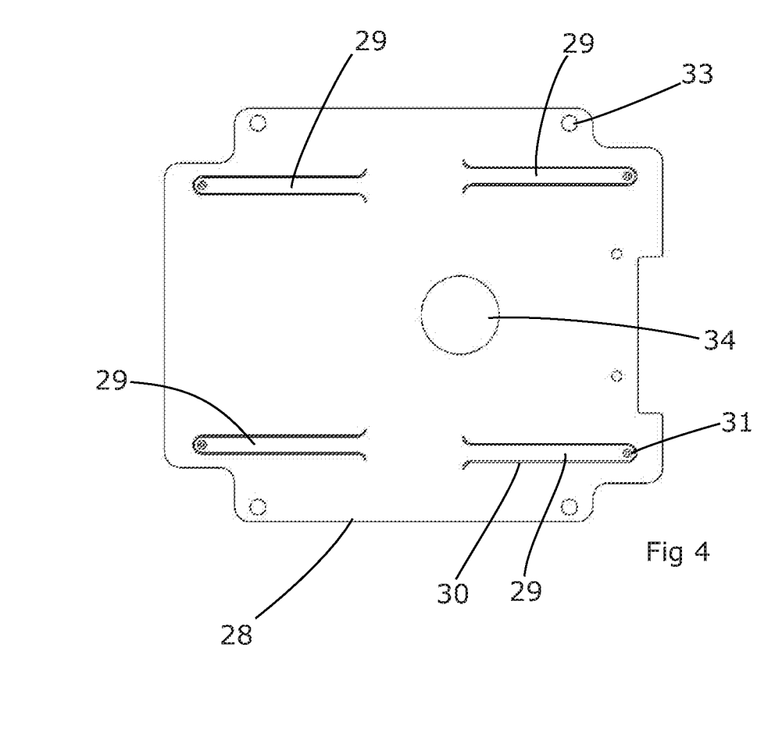
FIGS. 4 and 5 show a mounting spring for a touch-screen display in (respectively) plan and isometric form.
Figure 5:
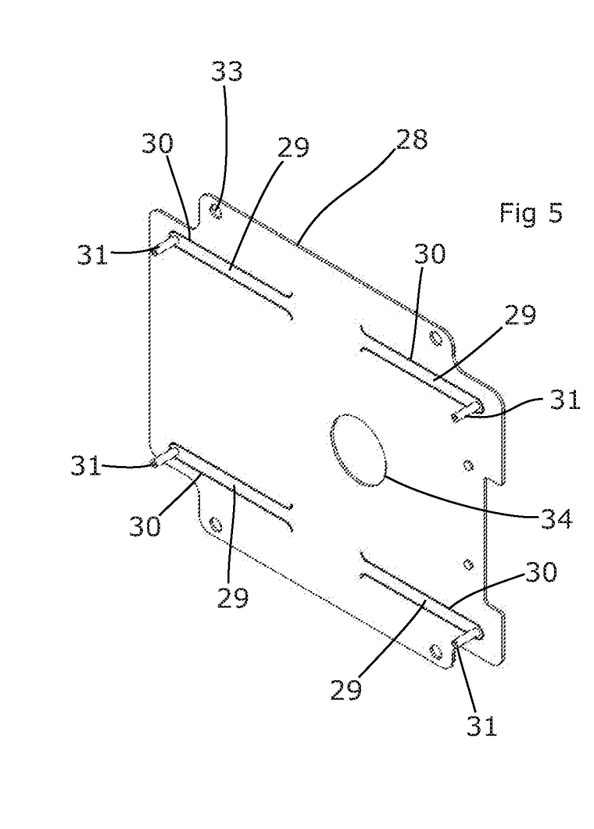
Figure 6:
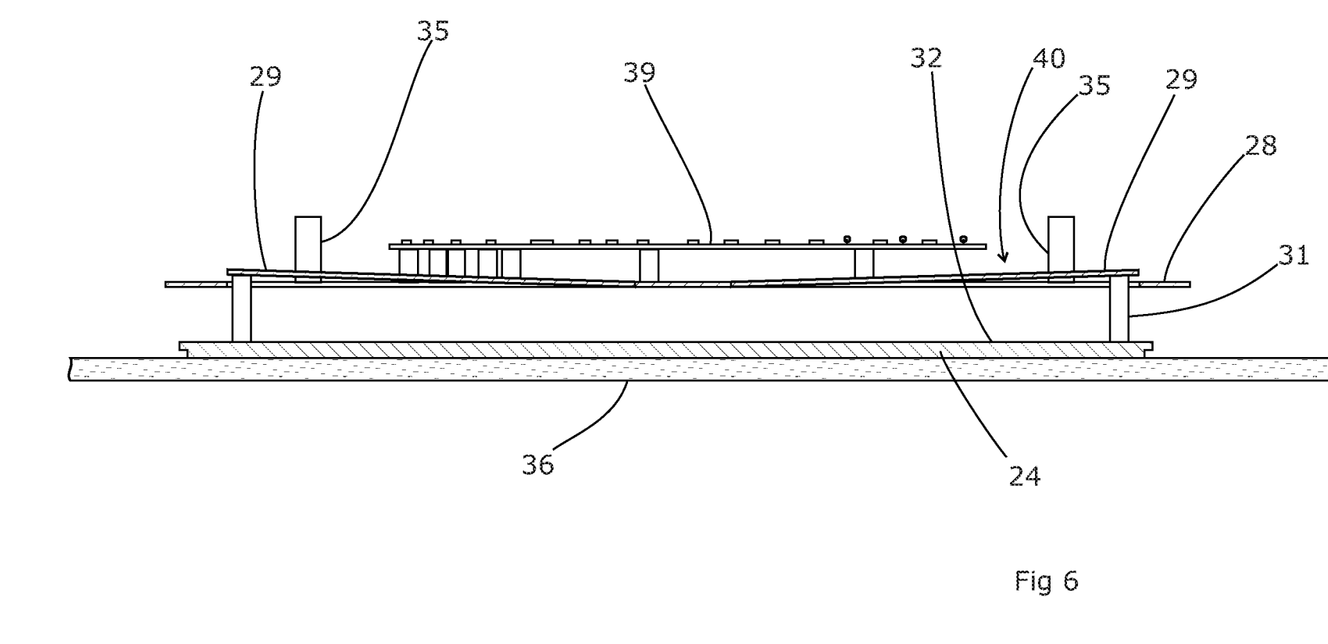
FIG. 6 shows a sectional view of a touchscreen device mounted using a spring according to FIGS. 4 and 5.

The touchscreen control panel 24 is affixed to the imaging and treatment system 6 in a mounting arrangement behind fascia 8 shown in FIGS. 4, 5 and 6. The fascia 8 obscures the components of the combined MRI and radiotherapy imaging and treatment system 6 from view by a patient or staff member 25 with the exception of the touchscreen control panel 24, as shown in FIGS. 1 to 3. The fascia 8 is thus opaque with a transparent region forming transparent cover 36 against which the touchscreen control panel 24 may be mounted. The fascia 8 may, of course, be completely transparent if desired. The fascia is preferably polycarbonate for ease of forming the curved profile with planar regions, but may equally be formed of any suitable material, including glass.

Although FIGS. 1 to 3 indicate a single touchscreen control panel 24, a plurality of touchscreen control panels may be present to enable control of a plurality of functions, by one or more staff members, or simply for the convenience of staff members as they move around the operational spaces 17. Up to four touchscreen control panels may be visible to staff members positioned in one or both of the operation spaces 17. A plurality of transparent regions will be provided accordingly.

A retaining structure 40 is provided between the transparent cover 36 and the touchscreen control panel 24 to affix the touchscreen control panel 24 against the rear face of the transparent cover 36. A staff member 25 may input commands to the touchscreen control panel 24 through the transparent cover 36 by touching the screen. The retaining structure 40 is comprised of a chassis 28 in the form of a plate that, in use, is mounted substantially parallel to the transparent cover 36 and the rear face 32 of the touchscreen control panel 24. The chassis 28 is removably mounted to the imaging and treatment system 6 using standard fixings 35 and is thus provided with fixing apertures 33. A service aperture 34 is formed to accommodate power supply and other wired connections typically required for communication between a printed circuit board (PCB) 39 and the touchscreen control panel 24, as shown in FIG. 6. Alternatively, the touchscreen control panel 24 can be a tablet or other touch screen controlled electronic device. A touchscreen control panel 24 is preferred, to allow networked control by the control unit of the main control terminal 23 via PCB 39.

Slots 30 in the chassis 28 define elongate fingers 29 arranged in a symmetrical pattern. At an end part of each finger 29, a protrusion 31 extends from the finger 29 toward the rear face of the touchscreen control panel 24. Each protrusion 31 attaches to the rear face of the touchscreen control panel 24, permanently or removably. The or each protrusion 31 is a rigid member with a depth greater than the spacing between the chassis 28 and the rear face 32 of the touchscreen control panel 24. When the touchscreen control panel 24 is mounted, the protrusion 31 acts as a spacer causing the end part of the associated finger 29 to move out of the plane of the chassis 28 such that the finger 29 is retained at an acute angle to the plane of the chassis 28. The chassis 28 is formed of a suitable material appropriately dimensioned to enable cooperation between finger 29 and its associated protrusion 31 to provide a resilient biasing force against the rear face of the touchscreen control panel 24 such that the touchscreen control panel 24 bears against the rear face of the transparent cover 36.

The arrangement of finger 29 and its associated protrusion 31 provides shock absorbance in the event that impact or undue pressure is applied to the fascia 8. In such instances, the touchscreen control panel 24 can move away from the fascia 8 this preventing damage to the touchscreen control panel 24. The fascia 8 may be replaced independently of the touchscreen control panel 24, and vice versa. It will of course be understood that many variations may be made to the above-described embodiment without departing from the scope of the present invention.

The touchscreen control panel may be integrated into a tablet device or small computing device that is mounted to the retaining structure in a similar manner to that described in the above defined embodiment. The tablet device may be battery or mains powered. The tablet device may be networked to the main control terminal 23 so as to send and/or receive information from the main control terminal. The tablet device may receive signals from the control unit, or may not be networked In a further embodiment, a screen or display may be provided in place of a touch screen control panel. Said display may be present to convey information to the staff member and/or patient.

The protrusion may be formed of a rigid material or a resilient material. The protrusion may be a spring dimensioned such that the length of the spring in compressed form is greater than the spacing between the chassis and rear face of the control panel when the chassis and control panel are mounted.

The invention claimed is:

1. A mounting arrangement for a display device comprising a display panel, the mounting arrangement comprising:
   a cover having a transparent section arranged for receiving the display panel against a rear face of the transparent section so as to be visible through a front face of the transparent section, and
   a retaining structure for holding the display panel in place, the retaining structure comprising a chassis fixable in position relative to the cover, the chassis having at least one resilient finger arranged to extend therefrom alongside a rear face of the display panel, wherein:
   a part of the at least one resilient finger is arranged to bear against the rear face of the display panel to resiliently urge the display panel against the rear face of the transparent section of the cover when the display panel is received by the cover; and
   the retaining structure is removably mounted to an external component independently of both the cover and the display panel.

2. The mounting arrangement according to claim 1, in which the at least one resilient finger includes a protrusion which bears on the rear face of the display panel.

3. The mounting arrangement according to claim 2, wherein the protrusion causes an end part of an associated finger to move out of a plane of the retaining structure, such that the associated finger is retained at an acute angle to the plane of the retaining structure when the display panel is received by the cover.

4. The mounting arrangement according to claim 3, wherein the mounting arrangement further comprises the display device, in which the display device is a control panel.

5. The mounting arrangement according to claim 2, in which the protrusion has a depth greater than a space between the chassis and the rear face of the display panel when the chassis and display panel are mounted.

6. The mounting arrangement according to claim 2, in which the protrusion is at an end part of the resilient finger.

7. The mounting arrangement according to claim 1, in which the chassis comprises at least an additional resilient finger.

8. The mounting arrangement according to claim 7, in which the at least one resilient finger and the at least additional resilient finger are arranged in a symmetrical pattern.

9. The mounting arrangement according to claim 1, in which the chassis is a plate.

10. The mounting arrangement according to claim 9, in which the at least one resilient finger is a part of the plate defined by an arcuate slot formed in the plate.

11. The mounting arrangement according to claim 10, in which the slot has a U-shape.

12. The mounting arrangement according to claim 1, in which the cover is polycarbonate.

13. The mounting arrangement according to claim 1, in which the display panel is held in at least a direction parallel to a front face of the cover.

14. A radiotherapy apparatus comprising:
a display panel mounted on a mounting arrangement for a display device, the mounting arrangement comprising:
a cover having a transparent section arranged for receiving the display panel against a rear face of the transparent section so as to be visible through a front face of the transparent section, and a retaining structure for holding the display panel in place, the retaining structure comprising a chassis fixable in position relative to the cover, the chassis having at least one resilient finger extending therefrom alongside a rear face of the display panel, a part of the at least one resilient finger is arranged to bear against the rear face of the display panel to resiliently urge the display panel against the rear face of the transparent section of the cover when the display panel is received by the cover, the retaining structure being removably mounted to the radiotherapy apparatus independently of both the cover and the display panel.

15. The radiotherapy apparatus of claim 14, the retaining structure being removably mounted as a whole relative to the cover, wherein the display device is a touch-screen device.

16. The radiotherapy apparatus of claim 14, in which the display device is a control panel.

17. The radiotherapy apparatus of claim 14, in which the at least one resilient finger includes a protrusion which bears on the rear face of the display panel.

18. The radiotherapy apparatus of claim 17, wherein the protrusion causes an end part of an associated finger to move out of a plane of the retaining structure, such that the associated finger is retained at an acute angle to the plane of the retaining structure when the display panel is received by the cover.

19. The radiotherapy apparatus of claim 17, in which the protrusion has a depth greater than a space between the chassis and the rear face of the display panel when the chassis and display panel are mounted.

20. The radiotherapy apparatus of claim 17, in which the protrusion is at an end part of the resilient finger.

\* \* \* \* \*